United States Patent [19]
Laird et al.

[11] Patent Number: 5,599,464
[45] Date of Patent: Feb. 4, 1997

[54] FORMATION OF ATOMIC SCALE VERTICAL FEATURES FOR TOPOGRAPHIC INSTRUMENT CALIBRATION

[75] Inventors: Ellen R. Laird, San Jose; W. Murray Bullis, Sunnyvale; James J. Greed, Jr., Los Gatos; Bradley W. Scheer, San Jose, all of Calif.

[73] Assignee: VLSI Standards, Inc., San Jose, Calif.

[21] Appl. No.: 539,973

[22] Filed: Oct. 6, 1995

[51] Int. Cl.$^6$ .................................................. C03C 15/00
[52] U.S. Cl. .................................................. 216/2; 216/11
[58] Field of Search ............................ 156/628.1, 644.1, 156/662.1; 216/2, 11, 62, 79, 87, 99; 73/1 J, 105

[56] References Cited

U.S. PATENT DOCUMENTS

| | | | |
|---|---|---|---|
| 4,386,850 | 6/1983 | Leahy | 356/243 |
| 4,597,665 | 7/1986 | Galbraith et al. | 356/237 |
| 4,615,762 | 10/1986 | Jastrzebski et al. | 156/628.1 |
| 5,169,488 | 12/1992 | Giuffre et al. | 216/2 |
| 5,198,869 | 3/1993 | Monteverde et al. | 356/243 |
| 5,332,470 | 7/1994 | Crotti | 216/79 |
| 5,520,769 | 5/1996 | Barrett et al. | 156/628.1 |

FOREIGN PATENT DOCUMENTS

| | | |
|---|---|---|
| 1-20428A | 1/1989 | Japan . |
| 4-289411 | 10/1992 | Japan . |

OTHER PUBLICATIONS

Hitchman, M. L. et al. "Calibration Standards for surface profile monitors" J. Phys. E vol. 13 (1), pp. 19–20 Jan. 1980.
Ohmi, T. et al. "Calibration of height in atomic force mecroscope images with subnanometer scale silicon dioxide steps" Appl. Phys. Lett. vol. 61, No. 20, pp. 2479–2481 Nov. 1992.
Candela et al. "Film thickness and refractive index Standard Reference Material calibrated by ellipsometry and profilometry" SPIE vol. 661 Optical Testing and Metrology pp. 402–407 1986.

*Primary Examiner*—R. Bruce Breneman
*Assistant Examiner*—Anita Alanko
*Attorney, Agent, or Firm*—Thomas Schneck

[57] ABSTRACT

A calibration target for topographic inspection instruments, operating at sub-micrometer resolution levels, having features on the order of 10 Angstroms in vertical height, an atomic scale distance. The features are formed on a silicon substrate, such as a wafer, by deposition of a thick oxide, such as a typical thermal oxide, over the wafer surface. A pattern of features is patterned and etched to the level of raw silicon at the wafer surface. Areas which have been etched are converted to a thin oxide, which slightly lowers the level of silicon in these areas. All oxide is removed and the slightly lower level of silicon gives rise to features having atomic scale vertical topographic dimensions. Millions of such features are produced simultaneously on a wafer to mimic the effect of haze or micro-roughness on a polished wafer.

24 Claims, 4 Drawing Sheets

FORMATION OF ATOMIC SCALE VERTICAL FEATURES FOR TOPOGRAPHIC INSTRUMENT CALIBRATION

TECHNICAL FIELD

The present invention relates to methods for making calibration standards used to determine surface roughness, texture and haze in instruments such as optical surface scanners, mechanical profilers and scanning probe microscopes.

BACKGROUND ART

Frequently in semiconductor manufacturing, the starting quality of incoming silicon material may have a profound effect on the final electrical device quality. A silicon wafer characteristic of interest is surface micro-roughness, sometimes called "haze", measured by a topographic inspection device, such as a surface scanner. Surface roughness is of interest in other industrial manufacturing processes, such as disk and optical component fabrication, particularly with increasing demands for quality control. Since topographic inspection instruments function at various spatial bandwidths, with varying response functions, it has been difficult to characterize these instruments since each may be reporting a very different value from the same surface. The range of spatial wavelengths observed by the instrument generally means the data sampling rate per unit distance. Sometimes the spatial bandwidth is expressed as spatial frequency and computed from the one dimensional grating equation:

$$f = \frac{\sin\theta_s - \sin\theta_i}{\lambda} \quad \text{Eq. (1)}$$

where f is the spatial frequency, $\theta_i$ is the angle of incidence of a monochromatic light beam, $\theta_s$ is the principal scattering angle from the grating, and $\lambda$ is the wavelength of the beam. Alternatively, the ASTM has suggested a definition of spatial frequency in terms of a frequency range of a component of the Fourier transformed surface profile of an object. Calibration targets have been built to help obtain standard readings from some devices, particularly scanners. Such targets have been built to replicate haze patterns present on new, unpatterned, polished wafer surfaces.

The surface of a calibration target or standard should be extremely uniform and isotropic over a zone of interest, should be readily reproduced, and should have extremely small surface features to read the extremely low level values of haze which replicate the surface of prime silicon wafers. Such a haze standard was described by Scheer in U.S. Pat. No. 5,198,869, "Reference Wafer for Haze Calibration". The device described there however, envisions a haze standard that reads at a much higher level than would be useful for relating to a prime silicon wafer. The standard described was very useful but was comprised of two materials, one of which is a film layer causing additional effects from the optical path length differences through the film as well as phase shifts at the interfaces. Both of these effects will change with illumination wavelength and should therefore be eliminated. The reading device is a light collector of the type described in U.S. Pat. No. 4,597,665, assigned to Tencor Instruments, although other beam reading devices could be used. Various types of features have been used to simulate haze or roughness including pits, step height bars, line-space pairs and grid patterns. In most instances, these features were fabricated by photolithography on silicon substrates.

Calibration targets for another application of interest simulate a magnetic disk surface texture. Such targets must deal with a predominant mechanical effect that can reduce the reliability, or functionality, of disk recording media, referred to as stick-slip, or, in its worst manifestation, blocking. Stick-slip is due to a high coefficient of friction that causes irregularities in the rotational speed of rigid recording disks. Since the system is dependent on a steady rate of data from the recording medium, stick-slip invariably will result in loss of data integrity. Blocking, on the other hand, can cause the heads to adhere completely to the disk surface. A final phenomenon, related to blocking, is called stiction and may be described as occasional blocking. This again will lead to premature mechanical wear.

All three of these effects may occur if the surfaces of the recording head or the media surface are too finely polished. To avoid these problems, a defined amount of surface texture must be imparted onto the surfaces themselves. This is known in the prior art. The amount of this imparted surface texture must be carefully controlled because it is desired to have the head in the required close proximity to the recording surface. This texture may be modelled with a calibration target and observed by a surface topographic inspection instrument.

Consequently, there is a need for a calibration target which models the tribological properties of the head-disk interface, particularly the surface topography of the disk coating.

An object of the invention was to devise a calibration target which would replicate the micro-roughness of highly polished wafer or disk surfaces at the lower limits of step height resolution, i.e. atomic distances.

SUMMARY OF INVENTION

The above object is achieved with a single material silicon calibration target having surface texture with feature heights on the order of 8Å to 100Å, but preferably atomic scale, about 10Å. Features having atomic scale vertical step heights are obtained by oxidation and etching of a silicon wafer. Oxygen atoms migrate into silicon, associating with silicon atoms of a substrate into silicon dioxide, allowing isolation of step heights having an atomic scale dimension. This is readily achieved with oxidation of silicon because an ambient reoxidation process is self-limiting at a given temperature, proceeding to a limited depth and then stopping. These atomic scale features are organized as arrays of pits or bars or a grid pattern, etc., in a major surface, typically planar, of the calibration target. Where pits have a random placement as described in U.S. Pat. No. 5,198,869, the calibration target is a haze standard.

The features may be formed in a thick oxide layer by first patterning the features, such as pits or stripes, using photoresist and a photomask. The areawise shape and distribution of the features is selected for mimicking the roughness of a test material to be scanned by a topographic measuring instrument. In one embodiment, the areas defined by the photomask pattern in the photoresist are etched into the thick oxide layer, so that the bare silicon is exposed in the etched areas. Next, a layer of thin oxide, e.g. native oxide, is formed in the etched areas when the bare silicon is exposed to an oxygen-rich environment. The silicon surface now contains shallow pits of atomic dimension in the previously patterned and etched areas. The height of these pits is only the distance to which the thin oxide extended into the substrate surface below the thick oxide. By clustering one million or more pits per square centimeter, with quasi-random placement, haze in wafer surfaces may be simulated for calibrating the lower limits of vertical resolution of an optical scanner.

Since the etched pits may be precisely located in known x–y coordinates as taught in U.S. Pat. No. 5,198,869, it is possible to replicate a given level of RMS roughness on a wafer's surface. The total etched area, combined with the etch depth, give roughness levels which are easily predicted mathematically. The derivation of this simple equation simply relates the etch depth, $\Delta z$, to the etched pit diameter, $d_p$, and the area of the scan, $A_{scan}$. If there is only one etched pit size, $A_{scan}$ is equal to the imaginary boxed area surrounding the pit. For n pit sizes, $(d_p=d_1, d_{p2}, \ldots, d_{pn})$ multiply n times $A_{scan}$ according to the following:

$$R_q = \Delta Z \left[ \frac{\pi}{4nA_{scan}} \sum_{i=1}^{n} d_{pi}^2 \right]^{1/2} \quad \text{Eq. (2)}$$

When using a single sized circular pit, a phenomenon known as Airy disk diffraction occurs when the pits are detected. This has the effect of producing pronounced dips in the PSD curve. Since the pit diameter is directly related to the Airy disk minima in the PSD curve, it is possible to directly find the pit diameters simply by relating the one-dimensional grating equation to the Airy disk equation. The utility of this is realized by including the area of this pit ($\pi d_p^2/4$) into the derived equation above. Since the scan area is known, the value of $\Delta z$, a very small step height, can be backed out directly. This is very useful for the calibration of very small vertical distances on atomic force microscopes.

However, this same phenomenon can be an interference when using this artifact to calibrate haze on a wafer scanning system. If the spatial bandwidth boundary of the scanner coincides with one of these minima, an additional uncertainty is added in the determination of haze. However, this can be dealt with directly in one of several ways: 1) by placing two pit diameters on the wafer's surface, alternating the two, one each in each adjoining "box", where the diameters are related by the multiples of the zeroth and first order Bessel functions (as contained in the Airy disk equation), then their resulting minima and maxima would overlap, thus smoothing out the PSD curve; 2) by using random sizes of pits within a given size range, the collective effect would also smooth out the PSD curve; and finally, 3) by etching these random pit sizes in close proximity, say three to a "box", each placed by a random vector which has a magnitude equal to the radius of the pit in that particular box, with the vector tail placed at the center of the initial pit placed in the box, then the final shape would not be circular, also eliminating any diffraction pattern. Each "box" is an imaginary section or grid square on the surface of a wafer as described in U.S. Pat. No. 5,198,869. Using the described technique, the etched areas have atomic scale vertical step heights, making it possible to characterize instruments such as atomic force microscopes, optical profilers, scanners and the like.

BEST MODE FOR CARRYING OUT THE INVENTION

Figure 1:
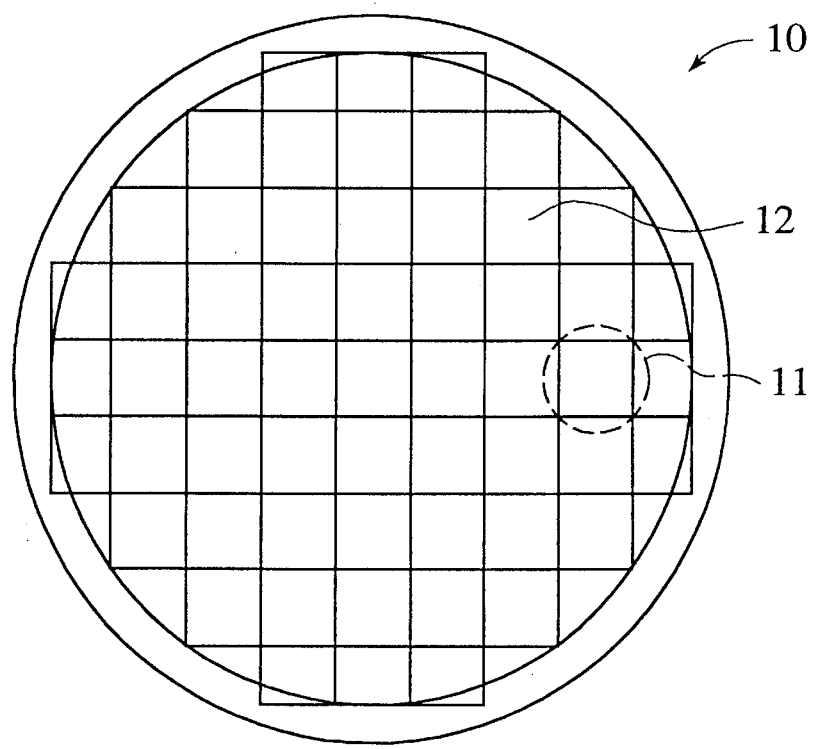
FIG. 1 is a top plan view of a calibration target in accord with the present invention.

With reference to FIG. 1, a silicon wafer 10 is shown divided into a plurality of imaginary sections 12. The wafer is a highly polished semiconductor substrate, i.e. a bare polished wafer. The sections 12 are not physically marked on the wafer and do not extend all the way to the edge of the wafer. The sections 12 are for the purpose of indicating that selected sections, such as a checkerboard pattern, could be used to contain features of the present invention. Alternatively, the entire surface may be covered with the features, which are designed to mimic the effect of haze on a highly polished wafer surface.

Figure 2:
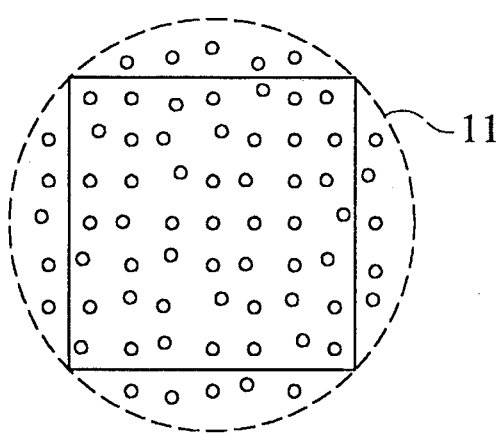
FIG. 2 is a magnification of a small portion of the calibration target of FIG. 1.

In FIG. 2, an enlargement of zone 11 of wafer 10 in FIG. 1 with the features placed in a quasi-random distribution, as indicated in U.S. Pat. No. 5,198,869 to simulate haze. For purposes of illustration, the density of features has been greatly reduced. The difference between the features described herein and the features described in U.S. Pat. No. 5,198,869 is that the features of the present invention have atomic scale step height or depth, on the order of about 10 Å, with a density of more than one million features per square centimeter. Placement of the features should be such that no interference pattern is formed by light scattered by the pattern in the presence of incident illumination.

Figure 3:
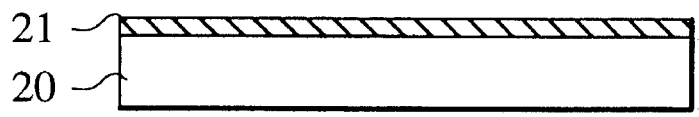
FIGS. 3–8 are side views of a microscopic portion of a calibration target, showing sectional views of a formation of a single feature in accord with the present invention.

In FIGS. 3–8, manufacture of a single feature is shown, but in practice, all of the features on the wafer, perhaps millions, would be made simultaneously. FIG. 3 shows a silicon wafer 20 having a uniform layer 21 of silicon dioxide thermally grown onto the silicon substrate. The silicon dioxide layer has a thickness of between 500Å and 1000Å. In the book Silicon Processing for the VLSI Era, vol. 1, p. 200–212, the thermal oxidation of silicon is explained. The book mentions that Deal and Grove described silicon oxidation as proceeding by the diffusion of an oxidant, such as molecular oxygen, through an existing oxide to the silicon-silicon dioxide interface, where molecules react with silicon to form silicon dioxide. In other words, oxygen migrates to the bare silicon substrate, where it interacts with silicon, thereby lowering the level of the silicon/silicon dioxide interface in places where oxidation has occurred. This is a key aspect of the present invention.

Figure 4:
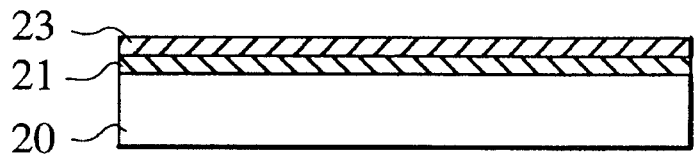

In FIG. 4, a thin layer 23 of positive photoresist is applied. The photoresist may be patterned 10 with the desired location, areawise extent and overall density of features by means of a mask. When light is used to expose the photoresist layer 23 through the mask, a latent image of the features is formed in the photoresist by light. In other words, the chemical bonds in the exposed photoresist are broken, altering the molecular weight and solubility of the resist, which allows the latent image to be developed, removing the exposed photoresist in the etched area, uncovering the underlying silicon dioxide layer. In the case of positive photoresist, the bonds of the exposed photoresist are broken.

Figure 5:
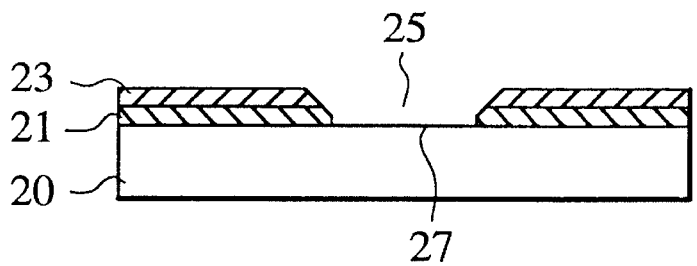

In FIG. 5, portions of the resist layer 23, now removed, create an aperture 25 where the resist has been exposed by light. An oxide etchant is used to remove silicon dioxide down to the upper surface 27 of the silicon substrate 20, which is uniformly lower than the original level.

Figure 6:
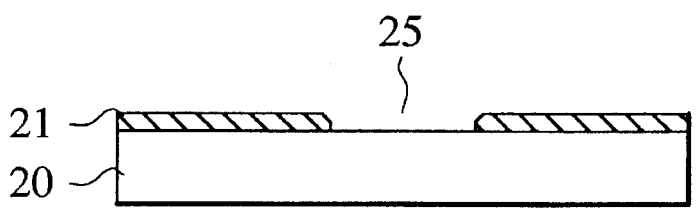
Figure 7:
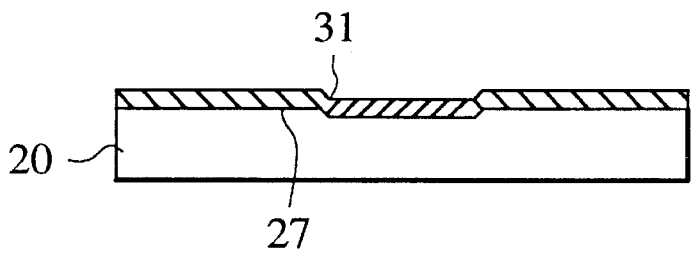

In FIG. 6, the photoresist is stripped from the oxide layer 21. The aperture region 25, now a single pit 31 in an array of similar pits which will form topographic features, including the light scattering features of the present invention, undergo self-limiting reoxidation due to exposure to air. Any oxidizing ambient environment could be used, but air is effective and inexpensive. Air oxidation at room temperature produces native oxide which has a thickness of approximately 17Å. Approximately half of the native oxide layer consumes silicon at the substrate interface. This is shown in FIG. 7, where the native oxide at the bottom of a pit extends into the silicon substrate, below the former level 27 supporting the silicon dioxide. The formation of the native oxide layer is rapid, but generally stops by itself after a short time.

Figure 8:
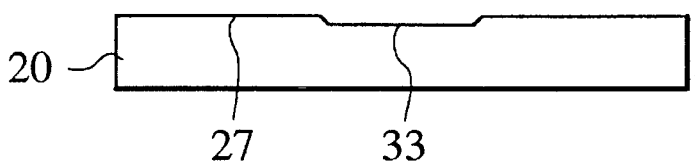

Next, all of the oxide is stripped, as shown in FIG. 8. It is now apparent that a differential step height exists between the bottom of the pit 33 and the former base 27 which supported the silicon dioxide.

In FIGS. 3–8, the construction of a topographic feature has been shown using a dark field mask, resulting in a pit within a light reflecting field. A reverse process could be used, producing a feature having a step height, rather than a pit. The reverse process could be achieved with reverse masks or with photoresist of the opposite type.

Figure 9:
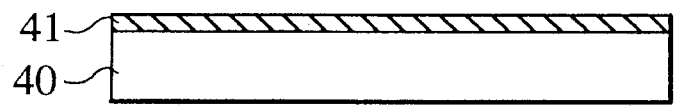
FIGS. 9–14 are side views of a microscopic portion of a calibration target, showing sectional views of an alternative formation method.

In FIG. 9, a uniform thermal oxide layer 41 is grown on a polished, light-reflective silicon wafer to a thickness which is between 700Å and 1000Å. Such layers are readily produced in the semiconductor industry with good consistency and uniform thickness over the surface of a wafer. Lesser thicknesses could be produced, but the range of 700Å to 1000Å is preferred because of the ease of manufacturing and of verifying the thickness with measuring instruments.

Figure 10:
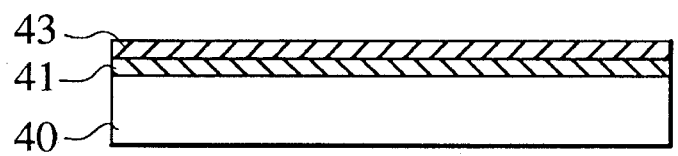

In FIG. 10, a layer of photoresist 43 is disposed over the thermal oxide layer 41. The photoresist is exposed to light through a mask which is the optical complement of the mask used for the exposure previously described with respect to FIGS. 4 and 5.

Figure 11:
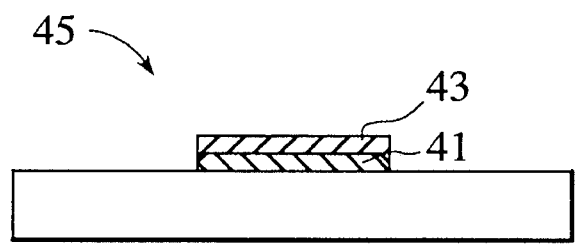
Figure 12:
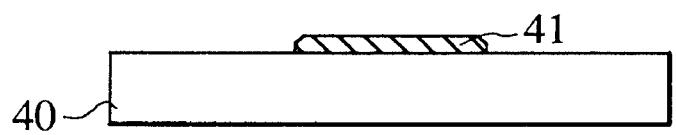

After removing the exposed portions of the photoresist and etching the oxide, a mesa is left, as shown in FIG. 11. The mesa 45 consists of a small layer of photoresist 43 atop a similarly sized layer of thermal oxide 41. In FIG. 12, the photoresist portion is shown to be stripped away.

Figure 13:
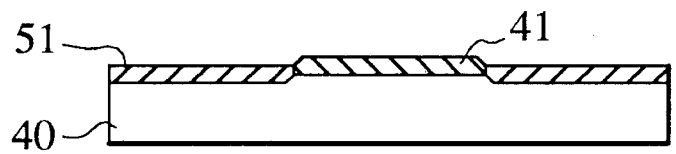
Figure 14:
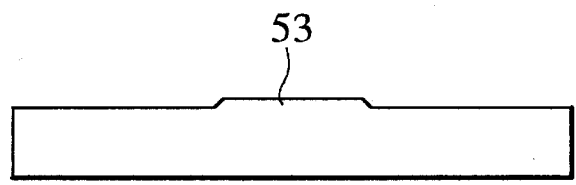

In FIG. 13, a very thin layer of native oxide 51 grows on the exposed silicon as air is allowed to be in contact with the wafer, consuming silicon below the initial wafer level. The silicon dioxide island 41 is removed, leaving a small mesa or feature 53, which also is exposed to air and has a uniformly thin native oxide layer. The feature 53 extends approximately 8Å to 9Å above the surface of the surrounding silicon field.

Laser scanners have a spatial resolution of approximately 50 micrometers. It is preferable to space the features described herein at approximately 1/10 this distance or every 5 microns. With a 100 μm typical beam diameter employed in a laser scanner, this means that approximately 300 pits are being illuminated at any given time. Therefore, it is not possible for the scanner to detect individual scattering features.

Figure 15:
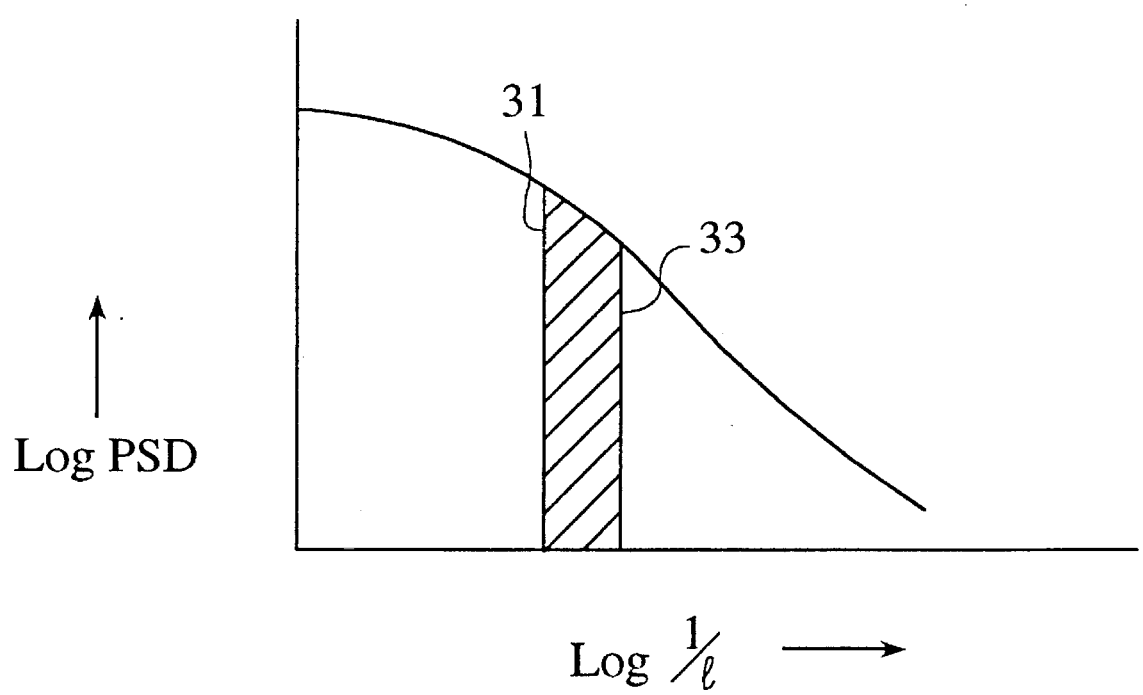
FIG. 15 is a graph depicting a one dimensional power spectral density curve of the isotropic calibration target shown in FIG. 1.

In calibrating a test instrument, the one-dimensional power spectral density curve for an isotropic calibration target is plotted. In FIG. 15, the logarithm of power spectral density (PSD), a quantity related to the amplitude of the detected light scattered or topographic amplitude detected from the feature, is plotted on the y-axis, while the spatial frequency 1/l, with l being spatial wavelength, is plotted along the x-axis (typically in inverse microns). The spatial wavelength l is the measure of the distance between surface peaks and valleys. For a given instrument, computed rms roughness, $R_{Q1}$, is defined as follows:

$$R_{Q1} = \sqrt{\int_{f_1}^{f_2} PSD(f)df} \qquad \text{Eq. (3)}$$

where $f_1$ and $f_2$ are the frequency limits of effective spatial bandwidth for that instrument, indicated by vertical lines 31 and 33 in FIG. 15, for a particular measuring instrument, and PSD is the power spectral density function. The shaded area under the curve is the square of the computed roughness value $R_{Q1}$. This value is defined in relation to $\Delta Z_i$, the variation from the mean surface level.

Different instruments will show different measured values of RMS roughness, $R_{QM}$, for the same calibration target, depending on the spatial bandwidth and response function of the instrument. The RMS roughness of a particular calibration standard, having a particular value of $\Delta Z_i$ chosen to obtain a value $R_q$ in the range of interest, becomes known as $R_{Q1}$ for a particular set of values for $f_1$ and $f_2$. For a particular instrument under test, $f_1$ and $f_2$ may be tested or determined readily from instrument attributes. If the instrument operates satisfactorily between $f_1$ and $f_2$ while testing the calibration target, and the measured $R_{QM}$ generally corresponds to the value $R_{Q1}$ calculated using equation (3), then the instrument is properly calibrated for detection of either a given microroughness value or a given haze level. Different targets, each with a different $\Delta Z_i$, may be used to establish the sensitivity of the instrument.

We claim:

1. A method of making a single material calibration target having atomic scale vertical topographic dimensions for testing instruments capable of measuring such dimensions comprising, providing a silicon wafer having a major surface and an array of apertures in a thick oxide layer deposited on the surface, the thickness of the layer exceeding 80 Angstroms, forming a thin oxide layer in said apertures, extending below the thick oxide layer by an atomic scale dimension, the thin oxide layer being substantially thinner than the thick oxide layer by a ratio of at least 10:1, and removing all oxide from the apertures and the surface, thereby leaving vertical topographic dimensions of atomic scale between the apertures and the surrounding regions.

2. A method of making a single material calibration target having atomic scale vertical topographic dimensions for testing instruments capable of measuring such dimensions comprising, providing a substrate having an upper surface made of a first material, forming a first layer of a second material by chemical combination of the second material with the first material, patterning the first layer of the second material with features separated from each other in a field, the features having an areawise shape and distribution for scattering light, creating the features by etching down through the second material to said first material while protecting the field, the features being apertures in the field, forming a second layer of the second material in said apertures, extending below the level of the first layer by an atomic scale amount, the second layer substantially thinner than the first layer, and removing all of the second material from the substrate.

3. The method of claim 2 wherein the substrate is a silicon wafer.

4. The method of claim 2 wherein said second material is silicon dioxide.

5. The method of claim 2 further defined by regrowing the second layer globally over the entirety of said substrate after removing all of the second material from the substrate.

6. The method of claim 2 wherein said first layer has a thickness in the range of between 500 and 2500 Angstroms.

7. The method of claim 2 wherein said second layer has a thickness in the range between 8 and 100 Angstroms.

8. The method of claim 2 wherein said atomic scale amount is less than 10 Angstroms.

9. The method of claim 2 wherein said feature have a density which exceeds one million features per square centimeter.

10. The method of claim 2 wherein said patterning step is by masking said body with photoresist and exposing said features with actinic radiation.

11. The method of claim 2 wherein said features are located in a regular pattern.

12. The method of claim 2 wherein said features are located in a quasi-random pattern.

13. The method of claim 2 wherein said features have different sizes.

14. The method of claim 13 wherein said feature sizes are random.

15. The method of claim 13 wherein said features are distributed in imaginary boxes over the substrate surface with alternating boxes each containing at least one feature of a size different from a neighboring box.

16. The method of claim 15 wherein the feature sizes are related as multiples of orders of Bessel functions.

17. A method of making single material calibration target having atomic scale vertical topographic dimensions for testing instruments capable of measuring such dimensions comprising, providing a silicon wafer having a major surface, forming a layer of thermal oxide on the wafer, patterning the thermal oxide layer with an array of features separated from each other in a field, etching through the silicon dioxide layer to bare silicon while protecting the field, the features being apertures in the field, forming a layer of native oxide in said apertures, extending below the level of the thermal oxide layer by an atomic scale step height dimension, the native oxide layer substantially thinner than the thermal oxide, and removing all oxide from the wafer thereby leaving features of having vertical topographic dimensions of atomic scale.

18. The method of claim 17 further defined by regrowing the native oxide globally over the entirety of said body after removing all oxide from the wafer.

19. The method of claim 17 wherein said thermal oxide layer has a thickness in the range between 8 and 100 Angstroms.

20. The method of claim 17 wherein said native oxide layer has a thickness in the range of between 8 and 50 Angstroms.

21. The method of claim 17 wherein said atomic scale amount is less than 10 Angstroms.

22. The method of claim 17 wherein said features have a density exceeding one million features per square centimeter.

23. The method of claim 17 wherein said patterning step is by masking said body with photoresist and exposing said features with actinic radiation.

24. The method of claim 17 wherein said features are located in a quasi-random pattern.

* * * * *

UNITED STATES PATENT AND TRADEMARK OFFICE
CERTIFICATE OF CORRECTION

PATENT NO : 5,599,464
DATED : Feb 4, 1997
INVENTOR(S): Ellen R. Laird et al.

It is certified that error appears in the above-identified patent and that said Letters Patent is hereby corrected as shown below:

Col. 3, line 12, "$(dp = d_1, d_{p2}, \ldots, d_{pn})$" should read -- $dp = d_{p1}, d_{p2}, \ldots, d_{pn})$ --.

Col. 4, line 49, "photoresist may be patterned 10 with the desired location" should read -- photoresist may be patterned with the desired location --.

Claim 9, col. 7, line 14, "said feature" should read -- said features --.

Signed and Sealed this

Eighth Day of July, 1997

Attest:

Attesting Officer

BRUCE LEHMAN

Commissioner of Patents and Trademarks